(12) United States Patent
Smith

(10) Patent No.: US 7,955,378 B2
(45) Date of Patent: *Jun. 7, 2011

(54) ENDOLUMINAL DEVICE AND SYSTEM AND METHOD FOR DETECTING A CHANGE IN PRESSURE DIFFERENTIAL ACROSS AN ENDOLUMINAL DEVICE

(75) Inventor: John K. Smith, Medford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 466 days.

This patent is subject to a terminal disclaimer.

(21) Appl. No.: 11/647,681

(22) Filed: Dec. 29, 2006

(65) Prior Publication Data

US 2007/0112413 A1 May 17, 2007

Related U.S. Application Data

(63) Continuation of application No. 10/143,434, filed on May 10, 2002, now Pat. No. 7,189,256.

(51) Int. Cl.
*A61F 2/82* (2006.01)
(52) U.S. Cl. ...................................... 623/1.34; 623/1.13
(58) Field of Classification Search .................. 623/1.13, 623/1.34
See application file for complete search history.

(56) References Cited

U.S. PATENT DOCUMENTS

| | | | |
|---|---|---|---|
| 5,078,736 A | 1/1992 | Behl | |
| 5,123,917 A | 6/1992 | Lee | |
| 5,824,042 A | 10/1998 | Lombardi et al. | |
| 6,077,297 A | 6/2000 | Robinson et al. | |
| 6,159,156 A | 12/2000 | Van Bockel | |
| 6,203,568 B1 * | 3/2001 | Lombardi et al. | 623/1.13 |
| 6,245,099 B1 | 6/2001 | Edwin et al. | |
| 6,285,739 B1 * | 9/2001 | Rudin et al. | 378/98.8 |
| 6,293,966 B1 | 9/2001 | Frantzen | |
| 6,334,868 B1 | 1/2002 | Ham | |
| 6,702,847 B2 | 3/2004 | DiCarlo | |
| 2002/0183628 A1 * | 12/2002 | Reich et al. | 600/486 |

FOREIGN PATENT DOCUMENTS

FR 2 714 816 7/1995

OTHER PUBLICATIONS

U.S. Appl. No. 09/896,864, filed Jun. 29, 2001, by Paul DiCarlo.
International Search Report for International Application No. PCT/US03/14690 mailed on Jun. 11, 2003.

* cited by examiner

*Primary Examiner* — Anhtuan T Nguyen
*Assistant Examiner* — Julie A Szpira
(74) *Attorney, Agent, or Firm* — Brooks, Cameron & Huebsch PLLC

(57) ABSTRACT

An endoluminal device for deployment in a body lumen includes a radially expandable stent, a graft attached to the stent, and a plurality of indicator members affixed to the graft and adapted to form a normal pattern in response to a normal pressure differential and an abnormal pattern in response to an abnormal pressure differential across the graft. By forming different patterns at different pressure differentials, the indicator members enable the detection of a change in pressure which could be evidence of a leak. A system for detecting a change in pressure differential includes the endoluminal device and an imaging system for displaying the indicator members. A method for detecting a change in pressure includes the steps of identifying the normal pattern, implanting the device, imaging the indicator members, and comparing the imaged pattern with the normal pattern to determine whether the normal pressure or an abnormal pressure differential exists.

19 Claims, 4 Drawing Sheets

ENDOLUMINAL DEVICE AND SYSTEM AND METHOD FOR DETECTING A CHANGE IN PRESSURE DIFFERENTIAL ACROSS AN ENDOLUMINAL DEVICE

CROSS REFERENCE TO RELATED APPLICATIONS

This is a Continuation Application of allowed U.S. patent application Ser. No. 10/143,434 filed on May 10, 2002 now U.S. Pat. No. 7,189,256.

TECHNICAL FIELD

This invention relates generally to endoluminal devices and, more specifically, to the detection of changes in pressure differential across such devices and the detection of leaks after implantation of such devices.

BACKGROUND OF THE INVENTION

An endoluminal device or prosthesis typically includes a stent and a fabric layer, or graft, supported by the stent. A stent is an elongated device which serves to affix the prosthesis in place by providing a radial force against a lumen wall, in addition to supporting the graft. The graft is typically made of a fabric or textile which has a low permeability with respect to the fluid, such as blood, flowing within the prosthesis. The graft may be fully supported by the stent along the entire length of the graft. Alternatively, the graft may have regions which are not directly supported by a stent or stent portion. The graft may be disposed radially outside or inside of the stent.

A prosthesis may be used to treat a vascular aneurysm by removing the pressure on a weakened part of an artery so as to reduce the risk of rupture. Typically, a prosthesis is implanted in a blood vessel at the site of an aneurysm endoluminally (i.e., by so-called "minimally invasive techniques") in which the prosthesis, restrained in a radially compressed configuration by a sheath or catheter, is delivered by a deployment system or "introducer" to the site where it is required. The introducer may enter the body through the patient's skin, or by a "cut down" technique in which the entry blood vessel is exposed by minor surgical means. When the introducer has been threaded into the body lumen to the prosthesis deployment location, the introducer is manipulated to cause the prosthesis to be ejected from the surrounding sheath or catheter in which it is restrained (or alternatively the surrounding sheath or catheter is retracted from the prosthesis), whereupon the prosthesis expands to a predetermined diameter at the deployment location, and the introducer is withdrawn. Stent expansion may be effected by spring elasticity, by balloon expansion, or by the self-expansion of a thermally or stress-induced return of a memory material to a pre-conditioned expanded configuration. Various types of stent architectures are known in the art, including many designs comprising a filament or number of filaments, such as a wire or wires, wound or braided into a particular configuration.

One common application for the implantation of prostheses is for treatment of abdominal aortic aneurysms (AAA). Such prostheses are typically placed into the aorta and iliac bifurcation with a covering to isolate the aneurysm from the blood. After the aneurysm has been isolated for some time, endoleaks may occur due to worn fabric or other reasons. For example, "type I endoleaks" are leaks occurring at the junction of the lumen wall and the most distal end of the prosthesis (i.e., furthest from the access point). Because the isolated aneurysm may become weak as a result of being isolated, once the leak starts, blood flow and pressure is slowly restored to the aneurysm, and the aneurysm may rupture. Currently, leaks are detected during follow-up angiograms and MRIs, but if the follow up visit does not coincide with the duration of time within which the leak must be treated, the undetected endoleak may result in a ruptured aneurysm that can be fatal to the patient.

Thus, prostheses placed into the vasculature divide the region of placement into a space that provides for the flow of blood and a space where blood flow is excluded. The prosthesis, therefore, is subjected to systolic blood pressure on the side exposed to blood flow (typically the inside surface of a prosthesis) and to some different pressure on the other side. In the treatment of aneurysms by use of a prosthesis, the elimination of growth of the aneurysm sac depends upon the device reducing the pressure on the outside of the prosthesis relative to the pressure on the inside of the prosthesis. It is desirable to monitor this pressure differential to determine if the device has remained effective during its implantation period as a way of checking whether leaks have occurred.

Present attempts to measure pressures within aneurysms require the use of invasive procedures where transducers are introduced via catheters. The pressure measurement is taken relative to atmospheric pressure, so that the precision of the measurement is compromised by the need to operate over a range of absolute pressure from atmospheric up to systole. Thus, there is a need to aid in determining whether any leaks have occurred in a more precise and non-invasive manner.

SUMMARY OF THE INVENTION

According to an embodiment of the present invention, an endoluminal device for deployment in a body lumen comprises a radially expandable stent, a graft attached to the stent, and a plurality of indicator members affixed to the graft. The graft defines a radially interior space having an internal pressure and radially exterior space having an external pressure. The indicator members are adapted to form a normal pattern in response to a normal pressure differenial between the internal pressure and the external pressure and an abnormal pattern in response to an abnormal pressure differential between the internal pressure and the external pressure.

According to another embodiment of the present invention, a system for detecting a change in pressure differential across an implanted endoluminal device includes a plurality of indicator members and imaging means for displaying the plurality of indicator members. The device includes a radially expandable stent and a graft attached to the stent. The indicator members are affixed to the graft and are adapted to form a normal pattern in response to a normal pressure differential between the internal pressure and the external pressures, and an abnormal pattern in response to an abnormal pressure differential between the pressure and the external pressure.

According to another embodiment of the invention, a method for detecting a change in pressure differential across the device comprises the steps of: identifying a normal patter of a plurality of indicator members affixed to a graft of a device; implanting the device in the body lumen; imaging the plurality of indicator members to display an image pattern on the implanted device; and comparing the imaged pattern with the normal pattern to determine whether the normal pressure differential or the abnormal pressure differential exists.

BRIEF DESCRIPTION OF DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF INVENTION

The invention will next be illustrated with reference to the figures wherein similar numbers indicate the same elements in all figures. Such figures are intended to be illustrative rather than limiting and are included herewith to facilitate the explanation of the apparatus of the present invention.

Figure 1:
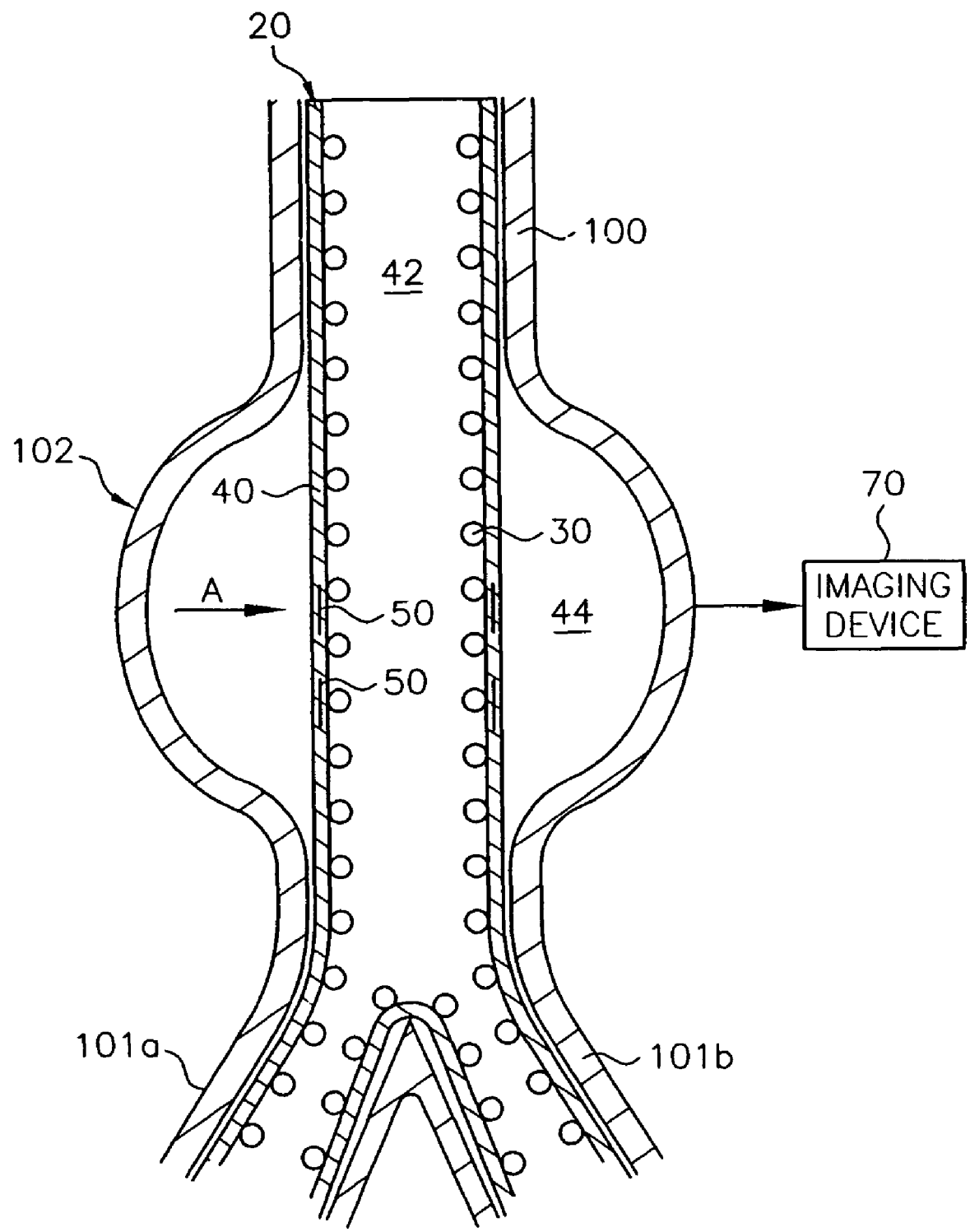
FIG. 1 is a longitudinal cross-sectional illustration of an aneurysm in a lumen and an exemplary endoluminal device of the present invention implanted therein and an exemplary system of the present invention for detecting a change in pressure differential across the implanted device.

FIG. 1 shows a partial cross-section of an endoluminal device 20 according to the present invention. Endoluminal device 20 can be implanted in a body lumen 100 in an area of an aneurysm 102. As shown, body lumen 100 is the aorta which branches into iliac arteries 101a and 101b; thus, in the embodiment shown in FIG. 1, endoluminal device 20 is a bifurcated endoluminal device, although the present invention contemplates the use of other types of endoluminal devices or prostheses in other body lumen.

The device includes a radially expandable stent 30, a graft 40 attached to the stent, plurality of indicator members 50 affixed to the graft. The configuration of the indicators members in a few exemplary embodiments are described in more detail below, in connection with FIGS. 2A-3B.

Radially expandable stent 30 may be any number of types of stents as are well known in the art. Various types of stents are known in the art, including many designs comprising a wire or wires, wound or braided into a particular configuration. Included among these stent configurations are braided stents such as described in U.S. Pat. No. 4,655,771 to Hans I. Wallsten, incorporated herein by reference. Another type of stent which may be used in connection with the present invention is that described in U.S. Pat. No. 5,609,627 to Goicoechea et al., also incorporated herein by reference. The stent used in connection with the present invention may have different configurations along its length, such as having a portion which is braided and another portion which is wound. The present invention could also be used with other types of stents, such as a laser cut stent. The stent may be balloon-expandable or self-expandable.

Figure 2A:
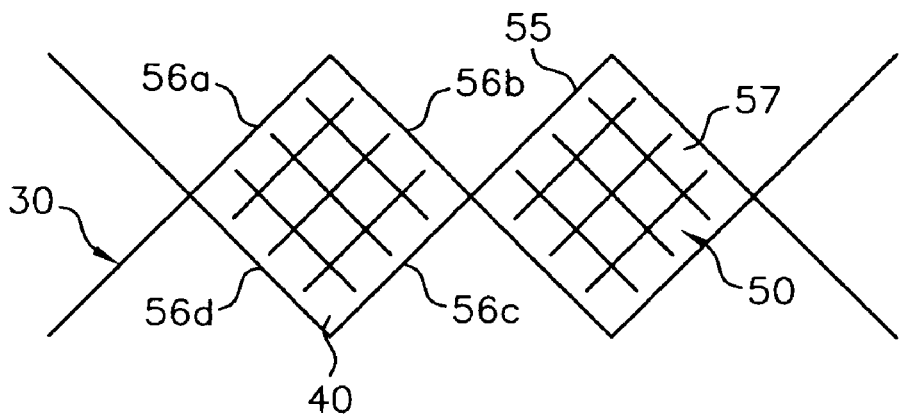
FIGS. 2A, 2B, and 2C are enlarged portions of embodiments of the endoluminal device according to the present invention, as viewed from the direction of arrow A, as shown in FIG. 1.
Figure 2B:
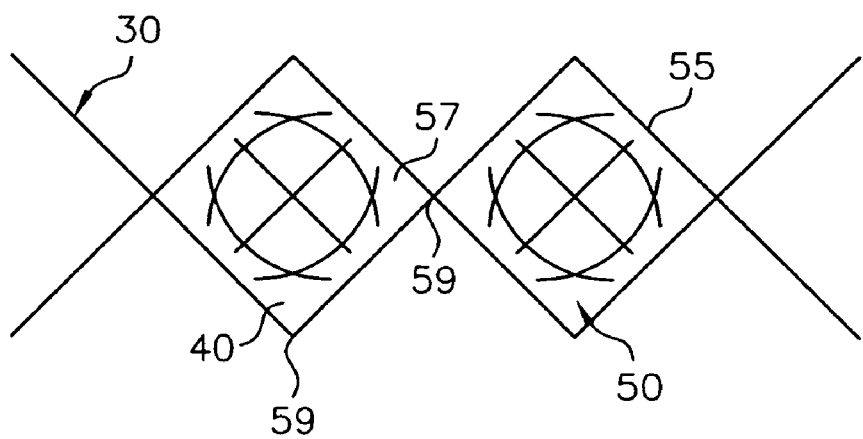
Figure 2C:
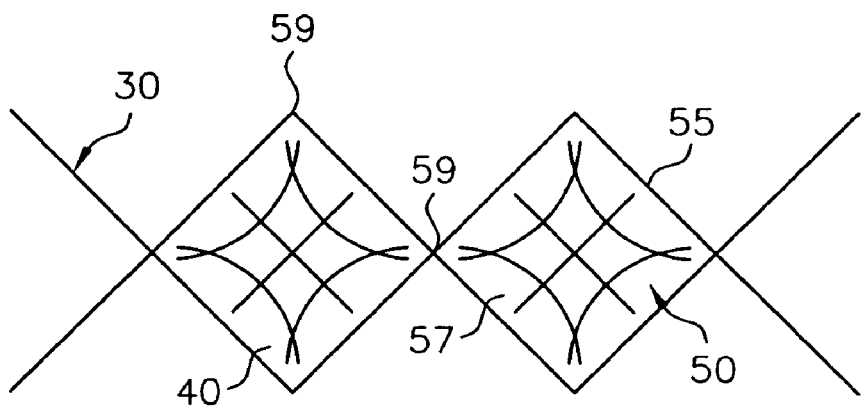

In the above stent configurations, the stent typically is made up of at least one metal wire 55, as shown in FIGS. 2A-2C. For reference, FIGS. 2A-2C are an enlarged portion of stent 30, graft 40, and indicator members 50. The view in FIGS. 2A-2C is from arrow A, as shown in FIG. 1, but could be any view taken from the outer circumference of device 20 looking radially inward towards the device. As shown best in FIGS. 2A-2C, wire 55 of stent 50 defines a number of openings 57. The openings are the portions of the graft 40 which are not directly engaged with wire 55. More specifically, stent 30 has a portion which defines a border of the openings, with the border being a plurality of edges, 56a-56d, as shown for example in FIG. 2A. In one embodiment of the invention, the stent selected is adapted to provide a plurality of openings, each having the same size regardless of the value of the differential pressure across the device. Such a stent could be, for example, a fairly rigid stent, such as a laser cut tube or a balloon-expandable stent.

Graft 40 may be of a material suitable for use as such grafts, as is well known in the art. Suitable graft materials include, but are not limited to, polyethyleneterepthalate (PET), polyetheretherketone (PEEK), polysulfone, polytetrafluroethylene (PTFE), expanded polytetrafluoroethylene (ePTFE), fluorinated ethylene propylene (FEP), polycarbonate urethane, a polyolefin (such as polypropylene, polyethylene, or high density polyethylene (HDPE)), silicone, and polyurethane. Yarns for braided grafts may comprise monofilaments or multifilament yarns, either with round or non-round cross-section, and multifilament yarns may comprise twisted or untwisted filaments. Thus, grafts may be of a non-woven material, such as PTFE, or could be of a woven, textile structure.

Graft 40 may be attached to stent 30 in a known way, for example by staples, suturing, or an adhesive, to name a few. Preferably, graft 40 is attached to stent 30 such that a predetermined configuration appears in the openings 57, as will be discussed in more detail below. One way of doing so is by attaching graft 40 to stent 30 at each junction 59 (as shown in FIGS. 2B and 2C) formed by the intersection of two edges, such as edges 56a and 56b or edges 56b and 56c. This method of attachment ensures that any pattern formed within opening 57 is properly spaced relative to the junctions 59 and the edges 56a-56d. Such attachment can be accomplished by staples or an adhesive at junctions 59. Alternatively, graft 40 may be attached to stent 30 by affixing the graft to the stent along the entire lengths of edges 56a-56d. This may be done most easily by using an adhesive. As shown in FIG. 1, graft 40 may be disposed radially outside of stent 30, but the graft may also be disposed radially within the stent. In either event, graft 40 defines a radially interior space 42 having an internal pressure and a radially exterior space 44 having an external pressure, as shown in FIG. 1. In the embodiment shown in FIG. 1, radially interior space 42 includes a flowpath for blood, while radially exterior space 44 is the aneurysm sac, which preferably should be isolated from the radially interior space by graft 40.

The endoluminal device 20 of the present invention also includes a plurality of indicator members 50 affixed to graft 40. As used herein, the term "affixed" shall mean attached in any way such as made integral with or appended to after individual assembly. As will be discussed in more detail below, for example in connection with FIGS. 2A-3B the plurality of indicator members 50 are adapted to form a normal pattern in response to a normal pressure differential between the internal pressure and the external pressure and an abnormal pattern in response to an abnormal pressure differential between the internal pressure and the external pressure.

As shown in FIGS. 2A-3B, the plurality of indicator members 50 are disposed at regions in graft 40 corresponding to at least one of the openings 57 of stent 30. In a first embodiment, the normal pattern formed by indicator members 50 is a plurality of lines disposed within opening 57 and parallel to each other and to a first of the edges 56a, as shown, for example, in FIG. 2A. More specifically, this normal pattern includes three lines which are parallel to edges 56a and 56c, as well as three lines parallel to edges 56b and 56d. This pattern is made up of a central line and two outer lines, but other patterns could be used, such as patterns having more than one central line and more than two outer lines. The "normal pressure differential" referred to would be the pressure differential between systolic blood pressure occurring at radially interior space 42 and the pressure of the aneurysm sac at radially exterior space 44 in the absence of any leaks across the endoluminal device. These pressures can be easily determined by measurement, although this pressure differential will differ among patients. Accordingly, the lines can be affixed to graft 40 by forming, at no pressure differential across the graft, the central line substantially straight and the outer lines as curves bending towards the center of the first opening, as is shown in FIG. 2C. The degree of curvature necessary to achieve substantially straight lines when exposed to the normal pressure differential can be easily determined based on the resiliency of the graft material and the normal pressure differential.

According to another embodiment of the present invention, the indicator members 50 are affixed to the graft 40 by forming, at no pressure differential across the graft, a central line and two substantially straight lines parallel to each other and to an edge 56a, as shown in FIG. 2A. Once exposed to the normal pressure differential, the plurality of indicator members 50 should assume a normal pattern which, in this embodiment, is shown in FIG. 2B. Thus, the normal pattern according to this embodiment is a central line disposed within opening 57 and parallel to a first of the edges, such as edge 56a and two outer curves bending outwards from the center of the opening 57. In order to confirm that the normal pattern is achieved in this embodiment, a physician or medical technician can use a series of tracers with increasing degrees of curvature of the outer lines. In this way, the degree of curvature actually occurring in the patient can be compared with a number of calibrated indicator member tracers which correspond to various pressure differentials. Thus, once the tracer is found which most closely corresponds to the pattern which is actually being viewed, then the physician or medical technician can identify the actual pressure differential across the endoluminal device. Although this embodiment has the advantage that is easier to make the indicator member (merely as a straight line), it is somewhat more difficult to use in that a physician cannot just as easily detect "straight lines" to show a normal pattern, as in the first embodiment discussed above.

Figure 3A:
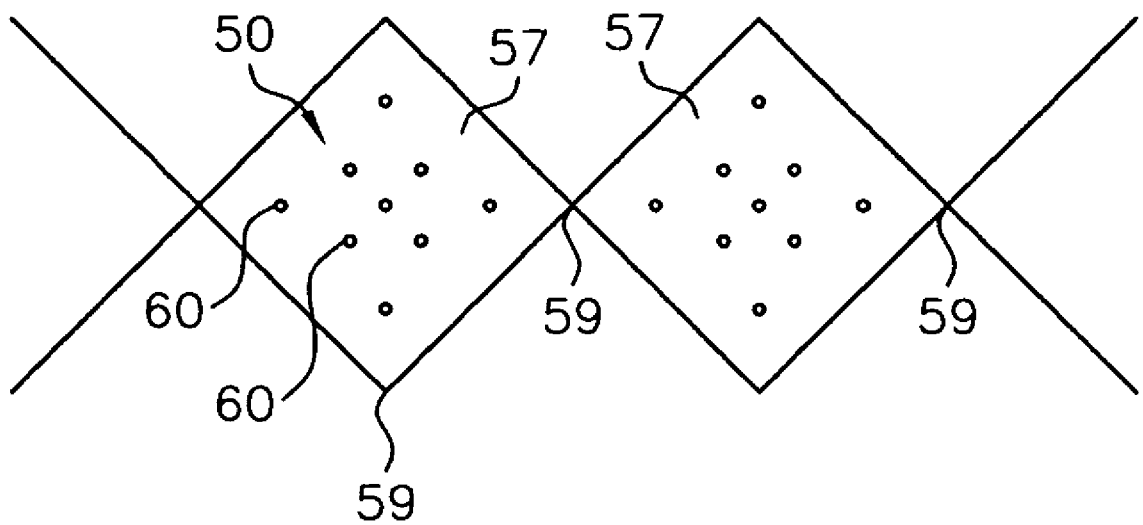
FIGS. 3A and 3B are enlarged portions of other embodiments of the endoluminal device according to the present invention, as viewed from the direction of arrow A, as shown in FIG. 1.
Figure 3B:
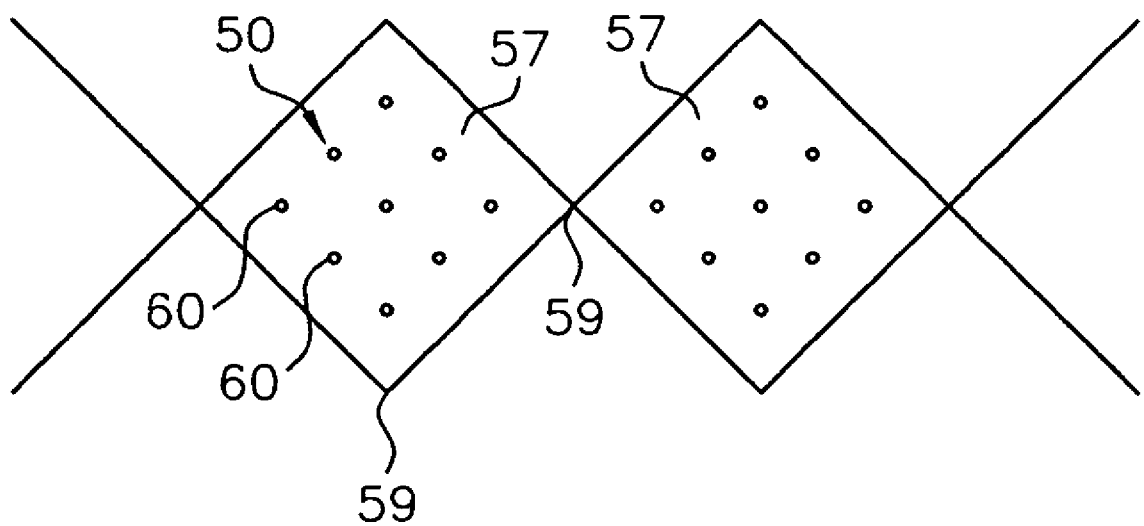

FIGS. 3A and 3B show an alternative embodiment of indicator members 50. In particular, as shown in FIG. 3B, the indicator members are dots 60. The indicator members are adapted to be positioned at regularly spaced intervals at the normal pressure differential in the normal pattern, as shown in FIG. 3B. This configuration is achieved by forming, at no pressure differential across graft 40, the indicator members as dots 60 in the configuration as shown in FIG. 3A. More specifically, the dots closer to junctions 59 are closer to the edges of the stent while the dots at the midpoints of each edge are closer to the center of the opening 57. As before, the degree to which the dots need to be moved depends on the normal pressure differential of the patient, which is a function of the patient's systolic blood pressure, as well as the degree of elasticity of the material of the graft.

The material used for the indicator members may be any known material which can be detected by use of an imaging device. For example, the indicator members may be a radiopaque material which is visualized by using an x-ray. Such radiopaque materials are well known, as described in U.S. patent application Ser. No. 09/896,864, entitled "ENDOLUMINAL DEVICE AND MONITORING SYSTEM FOR DETECTING ENDOLEAKS AND/OR CHANGES IN PROSTHESIS MORPHOLOGY," incorporated herein by reference. Any regular pattern can be appropriate in this invention. Moreover, the affixation of such indicator members to a graft are also well-known. For example, if a woven material is used as the graft material, one every tenth or fifteenth yarn may be a radiopaque material to form one of the patterns described above. In a device that uses a non-woven material as the graft material, such as ePTFE, the indicator members or markers can be attached to the covering by attaching metallic clips in a regular pattern onto the covering. It is also possible to mix into the ePTFE granules of metallic material.

The present invention also includes a system for detecting a change in pressure differential across an implanted endoluminal device between an internal pressure at a radially interior space and an external pressure at a radially exterior space. According to this system, the endoluminal device includes a radially expandable stent 30 and a graft 40 attached to the stent as well as a plurality of indicator members 50, as discussed above. The complete system is also shown in FIG. 1, which includes an imaging device 70. Imaging device may be any known device which can reveal a pattern of material formed in graft 40. For example, imaging device 70 may be an x-ray device where the material of the indicator members is a radiopaque material. Imaging device 70 may also be a magnetic resonance imaging device, an ultrasound device, or a CAT scan device.

A method of detecting a change in pressure differential across an endoluminal device between an internal pressure at radially interior space 42 and external pressure at radially exterior space 44 is also contemplated by the present invention. As before, the endoluminal device 20 includes a radially expandable stent 30, a graft 40 attached to the stent, and a plurality of indicator members 50 affixed to the graft. The indicator members 50 are adapted to form a normal pattern in response to a normal pressure differential between the internal pressure and the external pressure and an abnormal pattern in response to an abnormal pressure differential between the internal pressure and the external pressure.

Figure 4:
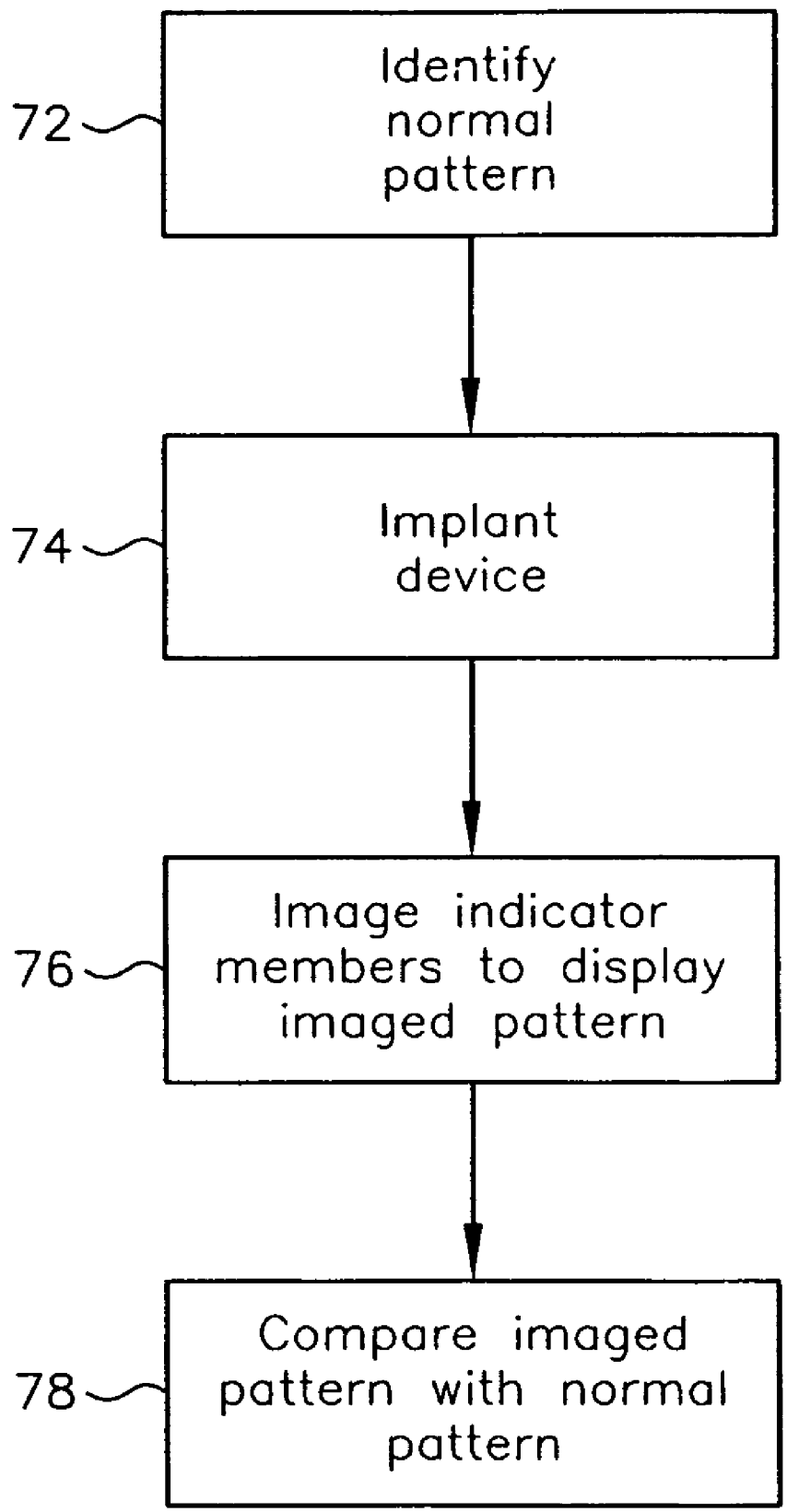
FIG. 4 is a flowchart showing the steps of the method for detecting a change in pressure differential across an endoluminal device according to the present invention.

The method for detecting a change in pressure differential is shown in FIG. 4. A first step 72 shown in FIG. 4 is to identify the normal pattern in response to the normal pressure differential between the internal pressure and the external pressure. As mentioned above, this contemplates determining what the normal pressure is both internal to and external to the graft. Typically, the normal pressure internal to the graft is the systolic blood pressure. In this invention, the systolic blood pressure is referred to as it is the highest blood pressure and it would be easiest to determine the shape of the indicator members at this highest blood pressure. This identifying step can be done outside of the body lumen by increasing the pressure inside of the graft until the proper pressure differential is achieved. An array of different endoluminal devices according to the present invention may be selected from, each having different degrees of curvature at no differential pressure across them such that one may be selected to achieve a series of substantially straight lines within each opening at the given pressure differential of the subject patient.

Next, in step 74, the endoluminal device is implanted in a body lumen. This can be done in a number ways as are well known in the art. U.S. Pat. No. 5,609,672 to Goicoechea et al., incorporated herein by reference, describes one such method of implantation. Preferably, before the endoluminal device is implanted in step 74, the normal pattern is recorded. This could be done manually or by taking an image, such as a digital image, of the indicator members at this normal pattern.

Next, the plurality of indicator members 50 are imaged in step 76, thus displaying an imaged pattern on the implanted endoluminal device. This is preferably done immediately after implantation. It may also be done in addition to, or alternatively to, immediately after implantation at some point in the future after implantation. The imaging step is done in a known manner, such as by using imaging means 70 as shown in FIG. 1. This could be as simple as using an x-ray device. When using an imaging device, it is important that the proper angle is used on the patient. Preferably, this angle should be as close to perpendicular to the central axis of the graft as is possible.

In step 78, the imaged pattern is compared with the normal pattern to determine whether the normal pressure differential or an abnormal pressure differential exists. In the treatment of aneurysms, the abnormal pressure differential is typically too low because of a leak. More specifically, because of a leak from the radially internal space 42 to the aneurysm sack in the radially external space 44, the pressure in the radially external space 44 increases. This causes a decrease in the pressure differential. Therefore, in an embodiment where the normal pattern is a series of straight lines, the pattern as actually viewed will be closer to that shown in FIG. 2C, with some concavity in the outer lines since the pressure differential is not as great as it should be. This comparison can either be done by a physician or a medical technician viewing the imaged pattern relative to the normal pattern, or by a digital comparison using a computer.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

For example, a prosthesis or endoluminal device of this invention may be any such prosthesis having at least one indicator member affixed to the graft that is adapted to be remotely monitored to indicate a change in pressure. The prosthesis may comprise any stent, graft, or stent-graft architecture known in the art, and is not limited to the exemplary designs shown herein. Although radiopaque markers are preferred embodiments, the indicator member may be any member capable of providing the desired result. The invention is not limited to the particular methods of analyzing information provided by the system discussed herein. Finally, the device and system may have other useful benefits beyond endoleak monitoring, and thus, the invention is not limited to any particular use.

What is claimed:

1. An endoluminal device for deployment in a body lumen, the device comprising:
   a radially expandable stent;
   a graft attached to said stent, wherein said graft has a radial interior exposed to an internal pressure and a radial exterior space exposed to an external pressure; and
   at least one indicator member affixed to said graft and adapted to form a first pattern within a single opening in the stent having a first degree of predetermined curvature in response to a first predetermined pressure differential between the internal pressure and the external pressure with the stent in an expanded configuration and a second pattern different from the first pattern within the single opening in the stent having a second degree of curvature in response to a second pressure differential between the internal pressure and the external pressure with the stent in an expanded configuration.

2. The endoluminal device according to claim 1, wherein said stent comprises a metal wire defining a plurality of openings and said at least one indicator member is positioned on said graft at regions corresponding to at least one of said openings.

3. The endoluminal device according to claim 2, wherein said stent has a portion defining a border of a first of said openings and said border comprises a plurality of edges, and said first pattern comprises a plurality of lines disposed within said first opening and parallel to each other and to a first of said edges.

4. The endoluminal device according to claim 3, wherein said plurality of lines include at least one central line and at least one outer line and said lines are affixed to said graft by forming, at no pressure differential across said graft, said at least one central line substantially straight and said plurality of outer lines as curves bending towards the center of said first opening.

5. The endoluminal device according to claim 2, wherein said stent has a portion defining a border of a first of said openings and said border comprises a plurality of edges, and said first pattern comprises at least one central line disposed within said first opening and parallel to a first of said edges and a plurality of outer curves bending outwards from the center of said first opening.

6. The endoluminal device according to claim 5, wherein said at least one indicator member is affixed to said graft by forming, at no pressure differential across said graft, said at least one central line and said plurality of outer curves as substantially straight lines parallel to each other and to said first edge.

7. The endoluminal device according to claim 2, wherein said at least one indicator member is a plurality of dots adapted to be positioned at regularly spaced intervals at the first pressure differential.

8. The endoluminal device according to claim 1, wherein said stent has a portion defining a border of a first of said openings and said border comprises a plurality of edges intersecting at least one junction, and said graft is attached to said stent at the at least one junction.

9. The endoluminal device according to claim 1, wherein said stent has a portion defining a border of a first of said openings and said border comprises a plurality of edges, and said graft is attached to said stent along the length of said edges.

10. The endoluminal device according to claim 9, wherein said graft is disposed radially outside of said stent.

11. The endoluminal device according to claim 1, wherein said stent is adapted to provide a plurality of openings, each having the same size regardless of the value of the differential pressure across said device.

12. The endoluminal device according to claim 11, wherein said stent is laser cut or filamentary.

13. The endoluminal device according to claim 1, wherein said graft is disposed radially within said stent.

14. The endoluminal device according to claim 1, wherein the device is adapted to be deployed to isolate an aneurysm having an aneurysm sac and the at least one indicator member is positioned on said graft at said aneurysm such that the external pressure is sac pressure.

15. The endoluminal device according to claim 1, wherein said at least one indicator member is made integral with said graft.

16. The endoluminal device according to claim 1, wherein said stent comprises a metal wire defining a plurality of openings and said at least one indicator member is positioned on said graft at regions corresponding to at least one of said openings, and wherein said stent has a portion defining a border of a first of said openings and said border comprises a plurality of edges, and said first pattern comprises a plurality of lines disposed within said first opening and parallel to each other and to a first of said edges.

17. The endoluminal device according to claim 1, wherein said first pattern is a normal pattern formed in response to a normal pressure differential between the internal pressure and the external pressure and said second pattern is an abnormal pattern formed in response to an abnormal pressure differential between the internal pressure and the external pressure.

18. A system for detecting a change in pressure differential across an implanted endoluminal device between an internal pressure corresponding to systolic blood pressure at a radially interior space and an external pressure corresponding to the pressure of an aneurysm sac at a radially exterior space, wherein said device comprises a radially expandable stent and a graft attached to said stent, the system comprising:
   a plurality of indicator members affixed to said graft and adapted to form a predetermined normal pattern within a single opening in the stent in response to a predetermined normal pressure differential between the internal pressure and the external pressure and an abnormal pattern different from the predetermined normal pattern within the single opening in the stent in response to an abnormal pressure differential between the internal pressure and the external pressure wherein the predetermined normal pressure differential is the pressure differential between the radially interior space and the radially exterior space in the absence of leaks across the device; and
   imaging means for displaying said plurality of indicator members.

19. The system according to claim 18, wherein said imaging means is selected from the group consisting of an x-ray device, a magnetic resonance imaging device, an ultrasound device, and a cat scan device.

\* \* \* \* \*